(12) United States Patent
Williams et al.

(10) Patent No.: US 9,493,770 B2
(45) Date of Patent: Nov. 15, 2016

(54) METHOD FOR IDENTIFYING ANTIBIOTIC TARGETS BY COMPLEMENTED SEQUENCING

(71) Applicant: DISCUVA LIMITED, Cambridge (GB)

(72) Inventors: David Hugh Williams, Cambridge (GB); Arthur Keith Turner, Cambridge (GB)

(73) Assignee: DISCUVA LIMITED, Cambridge (GB)

( * ) Notice: Subject to any disclaimer, the term of this patent is extended or adjusted under 35 U.S.C. 154(b) by 146 days.

(21) Appl. No.: 14/071,618

(22) Filed: Nov. 4, 2013

(65) Prior Publication Data

US 2014/0135234 A1 May 15, 2014

Related U.S. Application Data

(63) Continuation of application No. PCT/GB2012/000403, filed on May 3, 2012.

(51) Int. Cl.
*C40B 30/06* (2006.01)
*G06F 19/18* (2011.01)
*C12N 15/10* (2006.01)

(52) U.S. Cl.
CPC ......... *C12N 15/1082* (2013.01); *C12N 15/102* (2013.01); *C40B 30/06* (2013.01); *G06F 19/18* (2013.01)

(58) Field of Classification Search
None
See application file for complete search history.

(56) References Cited

U.S. PATENT DOCUMENTS

2002/0127562 A1* 9/2002 Shizuya .............. C12N 15/1082
435/6.13
2014/0141979 A1 5/2014 Williams et al.

FOREIGN PATENT DOCUMENTS

| EP | 1 188 829 | 3/2002 |
|---|---|---|
| WO | WO 99/50402 | 10/1999 |
| WO | WO 01/07651 | 2/2001 |
| WO | WO 02/00916 | 1/2002 |
| WO | WO 2004/018624 | 3/2004 |

OTHER PUBLICATIONS

International Search Report and Written Opinion mailed Sep. 25, 2012 for Application No. PCT/GB2012/000402.
International Search Report and Written Opinion mailed Sep. 25, 2012 for Application No. PCT/GB2012/000403.
[No Author Listed], NCBI Sequence Read Archive for SRA 026588. Submitted Nov. 23, 2010. http://www.ncbi.nlm.nih.gov/sra/?term=SRA026588. 4 pages.
Chen et al., Exploration of Drug Resistance Mechanism with EZ-Tn5 Transposome Insertion in Bacterial DNA. Chin J Nosocomiol. Dec. 31, 2010;20(13).
Ciampi et al., Transposon Tn10 provides a promoter for transcription of adjacent sequences. Proc Natl Acad Sci U S A. Aug. 1982;79(16):5016-20.
Danilchanka et al., Identification of a novel multidrug efflux pump of Mycobacterium tuberculosis. Antimicrob Agents Chemother. Jul. 2008;52(7):2503-11. doi: 10.1128/AAC.00298-08. Epub May 5, 2008.
Gallagher et al., Genome-scale identification of resistance functions in Pseudomonas aeruginosa using Tn-seq. MBio. Jan. 18, 2011;2(1):e00315-10. doi: 10.1128/mBio.00315-10. 8 pages.
Gawronski et al., Tracking insertion mutants within libraries by deep sequencing and a genome-wide screen for Haemophilus genes required in the lung. Proc Natl Acad Sci U S A. Sep. 22, 2009;106(38):16422-7. doi: 10.1073/pnas.0906627106. Epub Sep. 4, 2009.
Gerdes et al., Antimicrobial drug targets in vitamin biosynthetic pathways. Meeting Abstract. 41$^{st}$ Annual Meeting of the Interscience Conference on Antimicrobial Agents and Chemotherapy. Sep. 22-25, 2001, Illinois. 2001;41:247. Accession No. PREV200200565875. 2 pages.
Goodman et al., Identifying genetic determinants needed to establish a human gut symbiont in its habitat. Cell Host Microbe. Sep. 17, 2009;6(3):279-89. doi: 10.1016/j.chom.2009.08.003.
Judson et al., TnAraOut, a transposon-based approach to identify and characterize essential bacterial genes. Nat Biotechnol. Jul. 2000;18(7):740-5.
Judson et al., Transposon-based approaches to identify essential bacterial genes. Trends Microbiol. Nov. 2000;8(11):521-6. Review.
Kim et al., Essential genes in *Salmonella enteritidis* as identified by TnAraOut mutagenesis. Curr Microbiol. Oct. 2008;57(4):391-4. doi: 10.1007/s00284-008-9225-6. Epub Aug. 14, 2008.
Langridge et al., Simultaneous assay of every *Salmonella* Typhi gene using one million transposon mutants. Genome Res. Dec. 2009;19(12):2308-16. doi: 10.1101/gr.097097.109. Epub Oct. 13, 2009.
Lin et al., Systematic identification of genetic loci required for polymyxin resistance in Campylobacter jejuni using an efficient in vivo transposon mutagenesis system. Foodborne Pathog Dis. Mar. 2009;6(2):173-185. doi: 10.1089/fpd.2008.0177.

(Continued)

*Primary Examiner* — Karen S Weiler
(74) *Attorney, Agent, or Firm* — Wolf, Greenfield & Sacks, P.C.

(57) ABSTRACT

Provided herein are methods, and related compositions for identifying a putative essential gene which serves as an antibiotic target in a bacterium, the method, in some embodiments, comprising (a) generating an antibiotic resistant mutant of the bacterium by a method comprising the step of selecting for growth in the presence of an antibiotic to produce an antibiotic resistant mutant clone ($Ab^R$ mutant); (b) transforming the $Ab^R$ mutant with one or more essential genes of the bacterium and a transposon which insertionally inactivates bacterial DNA to produce a pool of transposon mutants which are merodiploid for the one or more essential genes; (c) growing bacteria from the merodiploid pool in the presence of different amounts of the antibiotic to produce two or more test cultures; and (d) comparing the distribution of transposon insertions between the test cultures to identify a putative essential gene serving as a target of the antibiotic in the bacterium.

18 Claims, 2 Drawing Sheets

(56) References Cited

OTHER PUBLICATIONS

Maus et al., Mutation of tlyA confers capreomycin resistance in Mycobacterium tuberculosis. Antimicrob Agents Chemother. Feb. 2005;49(2):571-7.

Patel et al., Overexpression of the rhamnose catabolism regulatory protein, RhaR: a novel mechanism for metronidazole resistance in Bacteroides thetaiotaomicron. J Antimicrob Chemother. Aug. 2009;64(2):267-73. doi: 10.1093/jac/dkp203. Epub Jun. 13, 2009.

Salipante et al., GeneHunter, a transposon tool for identification and isolation of cryptic antibiotic resistance genes. Antimicrob Agents Chemother. Dec. 2003;47(12):3840-5.

Schmid, Do targets limit antibiotic discovery? Nat Biotechnol. Apr. 2006;24(4):419-20.

Troeschel et al., Novel tools for the functional expression of metagenomic DNA. Methods Mol Biol. 2010;668:117-39. doi: 10.1007/978-1-60761-823-2_8.

Van Opijnen et al., Tn-seq: high-throughput parallel sequencing for fitness and genetic interaction studies in microorganisms. Nat Methods. Oct. 2009;6(10):767-72. doi: 10.1038/nmeth.1377. Epub Oct. 20, 2010. 17 pages.

Xu et al., [Bacterial promoter recognition and application]. Sheng Wu Gong Cheng Xue Bao. Chinese J Biotech Oct. 2010;26(10):1393-403. Review. Chinese.

Bordi et al., In vitro mutagenesis of Bacillus subtilis by using a modified Tn7 transposon with an outward-facing inducible promoter. Appl Environ Microbiol. Jun. 2008;74(11):3419-25. doi: 10.1128/AEM.00476-08. Epub Apr. 11, 2008.

Mikkelsen et al., Helper-Independent Sleeping Beauty transposon-transposase vectors for efficient nonviral gene delivery and persistent gene expression in vivo. Mol Ther. Oct. 2003;8(4):654-65.

\* cited by examiner

METHOD FOR IDENTIFYING ANTIBIOTIC TARGETS BY COMPLEMENTED SEQUENCING

RELATED APPLICATIONS

This application is a continuation of and claims the benefit under 35 U.S.C. §120 and §365(c) of International Application No. PCT/GB2012/000403, with an international filing date of May 3, 2012, and entitled "Method for Identifying Antibiotic Targets by Complemented Sequencing", the entire contents of which are herein incorporated by reference. This application also claims the benefit of Great Britain Patent Application No. 1107516.5, filed on May 5, 2011, the entire contents of which are herein incorporated by reference.

FIELD OF THE INVENTION

The present invention relates to methods for identifying an essential gene which serves as an antibiotic target in bacteria, to methods for identifying antibiotics and to processes for producing antibiotics and pharmaceutical compositions comprising said antibiotics.

BACKGROUND TO THE INVENTION

There is an urgent need for new antibiotics to counter the emergence of new pathogens and resistance to existing antimicrobial drugs. The identification of the targets of candidate antibiotics is critical, since such information can provide access to a large number of functionally related novel drug families. For example, the discovery of the penicillin-binding proteins as targets of penicillin led to the development of a large family of antibiotics, including multiple generations of cephalosporins, penicillins and carbapenems (see Schmid (2006) Nature Biotechnology 24(4): 419-420).

Transposon directed insertion-site sequencing (TraDIS—see Langridge et al. (2009) Genome Research 19: 2308-2316) has recently been described and used to identify: (a) essential genes; (b) genes advantageous (but not essential) for growth; (c) genes disadvantageous for growth under particular conditions; and (d) genes involved in conferring tolerance to certain conditions ("niche-specific" essential genes). Similar techniques have been described in e.g. Gawronski et al. (2009) PNAS 106: 16422-16427; Goodman et al. (2009) Cell Host Microbe 6: 279-289; van Opijnen et al. (2009) Nat. Methods 6: 767-772 and Gallagher et al. (2011) mBio 2(1):e00315-10, and such techniques are now collectively dubbed "Tn-seq" methods.

However, an important class of antibiotic targets are gene products involved in cellular processes essential for viability in the growth conditions used. Such targets cannot be identified by Tn-seq (including TraDIS), since transposon insertions into essential genes (including those serving as antibiotic targets) are not significantly represented in the initial mutant pool. Thus, differences in transposon distribution after growth of the mutant pool with or without (or with varying amounts of) antibiotic would not arise, with the result that Tn-seq cannot distinguish between an essential gene and an essential gene serving as an antibiotic target.

There is therefore a need for high-throughput functional screens for antibiotic targets which are capable of identifying essential genes serving as antibiotic targets.

SUMMARY OF THE INVENTION

According to an aspect of the present invention, there is provided a method for identifying an essential gene which serves as an antibiotic target in a bacterium, the method comprising the steps of:
(a) generating an antibiotic resistant mutant of said bacterium by a method comprising the step of selecting for growth in the presence of said antibiotic to produce an antibiotic resistant mutant clone ($Ab^R$ mutant);
(b) transforming the $Ab^R$ mutant with: (i) one or more essential genes of said bacterium; and (ii) a transposon which insertionally inactivates bacterial DNA, to produce a pool of transposon mutants which are merodiploid for said one or more essential genes and which bear transposon-mediated inactivated gene(s);
(c) growing bacteria from the merodiploid pool in the presence of different amounts of said antibiotic to produce two or more test cultures; and
(d) comparing the distribution of transposon insertions between test cultures to identify a putative essential gene serving as a target of said antibiotic in said bacterium.

Preferably, in step (b) the $Ab^R$ mutant is first transformed with vector DNA comprising the one or more essential genes of said bacterium. Further, in step (b) the $Ab^R$ mutant is first transformed with vector DNA comprising the one or more essential genes of said bacterium and then with the transposon. In such embodiments, the $Ab^R$ mutant may first be transformed with an extrachromosamal element (e.g. plasmid or BAC) comprising: (i) one or more essential genes of said bacterium; and (ii) one or more transposon repeat sequences; and then transformed (e.g. by conjugation with a donor bacterium) with a transposon delivery plasmid comprising: (i) a gene encoding a transposase; and (ii) invert repeat transposase recognition sites; wherein the one or more transposon repeat sequences of the extrachromosomal element confer transposon immunity against the transposon delivered by the transposon delivery plasmid.

The method may further comprise the steps of:
(a) generating a pool of mutant bacteria by transposon mutagenesis with an activating transposon ($Tn_A$), wherein the $Tn_A$ comprises a promoter such that transposon insertion into bacterial DNA increases the transcription of a gene at or near the insertion site;
(b) growing bacteria from the mutant pool in the presence of different amounts of said antibiotic to produce two or more test cultures; and
(c) comparing the distribution of $Tn_A$ insertions between test cultures to identify a putative essential gene serving as a target of said antibiotic in said bacterium.

In another aspect, there is provided a method of identifying an antibiotic comprising identifying an essential gene which serves as a target of said antibiotic according to a method of the invention.

In a further aspect, there is provided a process for producing an antibiotic comprising identifying an antibiotic by a method comprising identifying an essential gene which serves as a target of said antibiotic according to a method of the invention. Such a process may optionally further comprise the step of synthesising said antibiotic, and may optionally further comprise mixing the synthesised antibiotic with a pharmaceutically acceptable excipient to produce a pharmaceutical composition.

In a yet further aspect, there is provided a method for identifying a gene (for example an essential gene) which serves as an antibiotic target in a bacterium, the method comprising the steps of:

(a) transforming bacteria with an extrachromosamal element (e.g. plasmid or BAC) comprising: (i) one or more essential genes of said bacterium; and (ii) one or more transposon repeat sequences, to produce a pool of bacteria which are merodiploid for said one or more essential genes; and (b) transforming the merodiploids of step (a) with a transposon delivery plasmid comprising: (i) a gene encoding a transposase; and (ii) invert repeat transposase recognition sites;

wherein the one or more transposon repeat sequences of the extrachromosomal element of step (a) confer transposon immunity against the transposon delivered by the plasmid of step (b).

In a yet further aspect, there is provided a transposon delivery plasmid comprising: (i) a gene encoding a transposase; and (ii) invert repeat transposase recognition sites, for use in the method of the invention.

In another aspect, there is provided a kit comprising a transposon delivery plasmid comprising: (i) a gene encoding a transposase; and (ii) invert repeat transposase recognition sites, optionally further comprising a plasmid or BAC comprising: (i) one or more essential genes of a bacterium; and (ii) one or more transposon repeat sequences, which repeat sequences confer transposon immunity against the transposon delivered by the transposon delivery plasmid.

The use of transposon mutant pools generated from antibiotic resistant mutants which are merodiploid for one or more essential genes ensures that transposon insertions into essential genes (including those serving as antibiotic targets) are represented in the initial mutant pool, since transposon insertions into the antibiotic target gene yield viable phenotypes under non-selective conditions (when the wild type copy of the essential gene complements the insertionally inactivated mutant copy), but not under selective conditions (when the wild type copy does not complement the insertionally inactivated mutant copy).

Thus, differences in transposon distribution after growth of the merodiploid mutant pool with or without antibiotic can be readily detected, permitting identification of essential genes which serve as antibiotic targets.

Other aspects and preferred embodiments of the invention are defined and described in the other claims set out below.

DETAILED DESCRIPTION OF THE INVENTION

Figure 1:
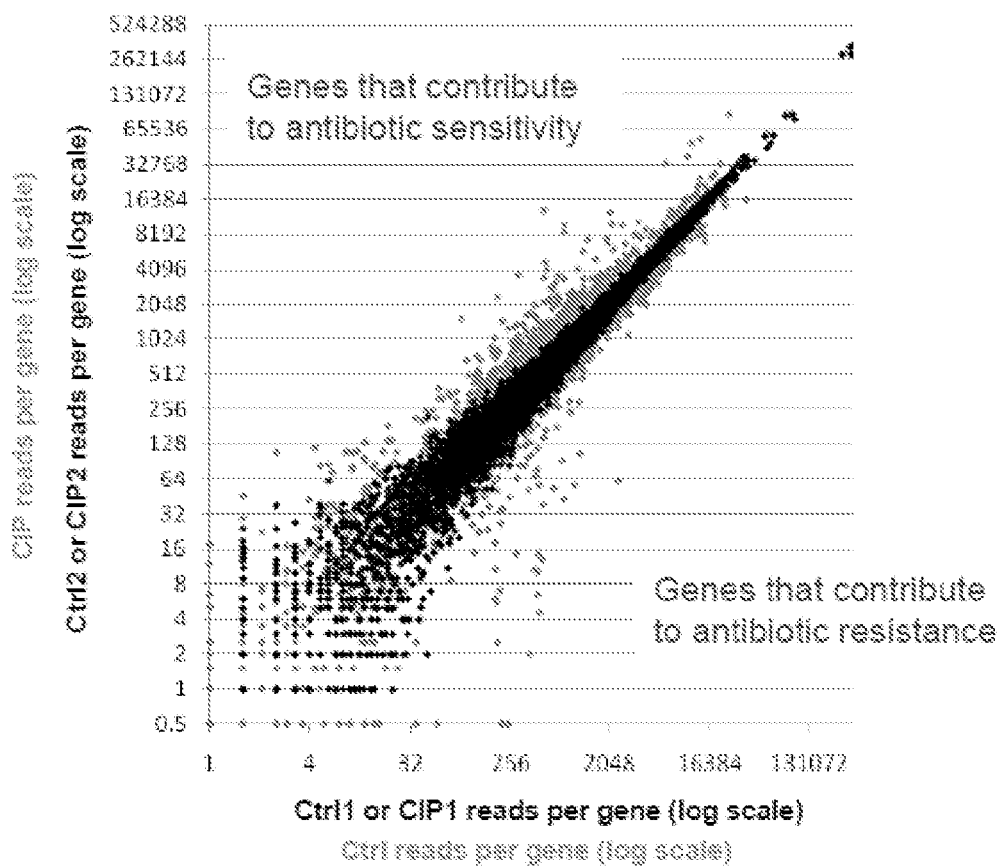
FIG. 1 shows a graph depicting the results of a pilot study to identify genes that contribute to ciprofloxacin resistance in *Salmonella Typhi*.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The term gene is a term describing a hereditary unit consisting of a sequence of DNA that occupies a specific location on a chromosome or plasmid and determines a particular characteristic in an organism. A gene may determine a characteristic of an organism by specifying a polypeptide chain that forms a protein or part of a protein (structural gene); or encode an RNA molecule; or regulate the operation of other genes or repress such operation; or affect phenotype by some other as yet undefined mechanism.

The terms genomic DNA is a term of art used herein to define chromosomal DNA as distinct from extrachromosomally-maintained plasmid DNA.

The term genome is a term of art used herein to define the entire genetic complement of an organism, and so includes chromosomal, plasmid, prophage and any other DNA.

The term Gram-positive bacterium is a term of art defining a particular class of bacteria that are grouped together on the basis of certain cell wall staining characteristics.

The term low G+C Gram-positive bacterium is a term of art defining a particular subclass class of evolutionarily related bacteria within the Gram-positives on the basis of the composition of the bases in the DNA. The subclass includes *Streptococcus* spp., *Staphylococcus* spp., *Listeria* spp., *Bacillus* spp., *Clostridium* spp., *Enterococcus* spp. and *Lactobacillus* spp.).

The term high G+C Gram-positive bacterium is a term of art defining a particular subclass class of evolutionarily related bacteria within the Gram-positives on the basis of the composition of the bases in the DNA. The subclass includes actinomycetes (actinobacteria) including *Actinomyces* spp., *Arthrobacter* spp., *Corynebacterium* spp., *Frankia* spp., *Micrococcus* spp., *Micromonospora* spp., *Mycobacterium* spp., *Nocardia* spp., *Propionibacterium* spp. and *Streptomyces* spp.

The term Gram-negative bacterium is a term of art defining a particular class of bacteria that are grouped together on the basis of certain cell wall staining characteristics. Examples of Gram-negative bacterial genera include *Klebsiella, Acinetobacter, Escherichia, Pseudomonas, Enterobacter* and *Neisseria.*

As used herein, the term "essential gene" is a term of art defining a particular class of genes the products of which are necessary for viability, either under all conditions or under the conditions of growth used. An important subclass of essential gene are those encoding products (e.g. proteins, peptides and regulatory polynucleotides) which contribute to metabolic processes essential for viability under important growth conditions (for example, and in the case of pathogenic bacteria, under conditions which prevail during infection or multiplication in the host).

Antibiotics and Antibiotic Targets

The antibiotic used to produce the test cultures of the invention is typically a novel investigational antibiotic (antibacterial chemotherapeutic agent), the mechanism of action (and hence biological target(s)) of which are unknown. In many applications, the antibiotic is selected from combinatorial libraries, natural product libraries, defined chemical entities, peptides, peptide mimetics and oligonucleotides.

The antibiotic target identified according to the invention is an essential gene/gene product, and may therefore be involved in one or more of the following biological processes in the bacterial host:

(a) cell division;
(b) DNA replication (including polymerization and supercoiling);
(c) transcription (including priming, elongation and termination);
(d) translation (including ribosome components, initiation, elongation and release);
(e) biosynthetic pathways (including peptidoglycan and fatty acids);
(f) plasmid addiction;
(g) cell wall assembly; and/or
(h) bacterial cell integrity.

Bacteria for Use in the Methods of the Invention

The methods of the invention may be applied to identify an antibiotic target in any bacterium. Thus, the methods of the invention find application in the identification of antibiotic targets in: (a) Gram-positive, Gram-negative and/or Gram-variable bacteria; (b) spore-forming bacteria; (c) non-spore forming bacteria; (d) filamentous bacteria; (e) intracellular bacteria; (f) obligate aerobes; (g) obligate anaerobes; (h) facultative anaerobes; (i) microaerophilic bacteria and/or (f) opportunistic bacterial pathogens.

In certain embodiments, the methods of the invention are applied to identify an antibiotic target in bacteria of the following genera: *Acinetobacter* (e.g. *A. baumannii*); *Aeromonas* (e.g. *A. hydrophila*); *Bacillus* (e.g. *B. anthracis*); *Bacteroides* (e.g. *B. fragilis*); *Bordetella* (e.g. *B. pertussis*); *Borrelia* (e.g. *B. burgdorferi*); *Brucella* (e.g. *B. abortus, B. canis, B. melitensis* and *B. suis*); *Burkholderia* (e.g. *B. cepacia* complex); *Campylobacter* (e.g. *C. jejuni*); *Chlamydia* (e.g. *C. trachomatis, C. suis* and *C. muridarum*); *Chlamydophila* (e.g. (e.g. *C. pneumoniae, C. pecorum, C. psittaci, C. abortus, C. felis* and *C. caviae*); *Citrobacter* (e.g. *C. freundii*); *Clostridium* (e.g. *C. botulinum, C. difficile, C. perfringens* and *C. tetani*); *Corynebacterium* (e.g. *C. diphteriae* and *C. glutamicum*); *Enterobacter* (e.g. *E. cloacae* and *E. aerogenes*); *Enterococcus* (e.g. *E. faecalis* and *E. faecium*); *Escherichia* (e.g. *E. coli*); *Flavobacterium; Francisella* (e.g. *F. tularensis*); *Fusobacterium* (e.g. *F. necrophorum*); *Haemophilus* (e.g. *H. somnus, H. influenzae* and *H. parainfluenzae*); *Helicobacter* (e.g. *H. pylori*); *Klebsiella* (e.g. *K. oxytoca* and *K. pneumoniae*), *Legionella* (e.g. *L. pneumophila*); *Leptospira* (e.g. *L. interrogans*); *Listeria* (e.g. *L. monocytogenes*); *Moraxella* (e.g. *M. catarrhalis*); *Morganella* (e.g. *M. morganii*); *Mycobacterium* (e.g. *M. leprae* and *M. tuberculosis*); *Mycoplasma* (e.g. *M. pneumoniae*); *Neisseria* (e.g. *N. gonorrhoeae* and *N. meningitidis*); *Pasteurella* (e.g. *P. multocida*); *Peptostreptococcus; Prevotella; Proteus* (e.g. *P. mirabilis* and *P. vulgaris*); *Pseudomonas* (e.g. *P. aeruginosa*); *Rickettsia* (e.g. *R. rickettsii*); *Salmonella* (e.g. serotypes *Typhi* and *Typhimurium*); *Serratia* (e.g. *S. marcesens*); *Shigella* (e.g. *S. flexnaria, S. dysenteriae* and *S. sonnei*); *Staphylococcus* (e.g. *S. aureus, S. haemolyticus, S. intermedius, S. epidermidis* and *S. saprophyticus*); *Stenotrophomonas* (e.g. *S. maltophila*); *Streptococcus* (e.g. *S. agalactiae, S. mutans, S. pneumoniae* and *S. pyogenes*); *Treponema* (e.g. *T. pallidum*); *Vibrio* (e.g. *V. cholerae*) and *Yersinia* (e.g. *Y. pestis*).

The methods of the invention may be used to identify an antibiotic target in multi-drug resistant bacteria, including, but not limited to penicillin-resistant, methicillin-resistant, quinolone-resistant, macrolide-resistant, and/or vancomycin-resistant bacterial strains, including for example penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant enterococci.

Thus, methods of the invention may be used to identify an antibiotic target in methicillin-resistant *Staphylococcus aureus* (MRSA), for example selected from any of C-MSRA1, C-MRSA2, C-MRSA3, C-MSRA4, Belgian MRSA, Swiss MRSA and any of the EMRSA strains.

The compounds of the invention may be used to identify an antibiotic target in both high G+C Gram-positive bacteria and in low G+C Gram-positive bacteria.

The methods of the invention find particular application in the identification of an antibiotic target in a bacterium selected from *Klebsiella pneumoniae, Acinetobacter baumanii, Escherichia coli* (including ST131), *Enterococcus faecalis, Enterococcus faecium, Pseudomonas aeruginosa, Enterobacter cloacae, Enterobacter aerogenes* and *Neisseria gonorrhoeae*.

Particularly preferred are methods of identifying an antibiotic target in *Klebsiella pneumoniae, Acinetobacter baumanii* or *Escherichia coli*.

Mutant Pools

The methods of the invention involve generating a pool of mutant bacteria by transposon mutagenesis. The size of the mutant pool affects the resolution of the method: as the pool size increases, more and more different genes with transposon insertions will be represented (and so effectively assayed). As the pool size decreases, the resolution of the method reduces, genes will be less effectively assayed, and more and more genes will not be assayed at all.

Ideally, the mutant pool generated in the methods of the invention is comprehensive, in the sense that insertions into every gene are represented (and preferably into several different sites in each and every gene). The number of transposon insertion mutants (i.e. the mutant pool size) required to achieve this depends on various factors, including: (a) the size of the bacterial genome; (b) the average size of the genes; and (c) any transposon insertion site bias.

With regard to the latter, some areas of bacterial genomes attract a low frequency of insertion (especially GC-rich regions). Thus, insertion frequencies and pool sizes large enough to ensure that insertions into insertion-refractory regions are preferred.

In general, a minimum insertion rate of one transposon per 25 bp is generally required to achieve a comprehensive pool/library, which typically entails a minimum pool size for bacteria having a genome size of 4 to 7 Mb of $0.5 \times 10^5$ to $1 \times 10^5$, for example $5 \times 10^5$, preferably at least about $1 \times 10^6$ mutants. In many cases, $1 \times 10^6$ mutants will allow identification of ~300,000 different insertion sites and correspond to 1 transposon insertion every 13 to 23 bp (or about 40-70 different insertion sites per gene).

However, the methods of the invention do not necessarily require a comprehensive mutant pool (in the sense defined above) in order to return useful information as to the identity of antibiotic drug targets. Rather, pool sizes less than the ideal comprehensive pool may be used, provided that a reduction in resolution (and attendant failure to assay certain genes) can be tolerated. This may be the case, for example, where the method is designed to be run iteratively until the target is identified: in such embodiments the effective pool size grows with each iteration of the method.

Creation of Merodiploids

Several methods are available for the creation of the merodiploid state in the methods of the invention. These include, without limitation: (a) the creation of a duplicated region of the bacterial chromosome by insertion using a suicide vector; (b) the creation of a duplicated region of the bacterial chromosome by insertion using an integrative plasmid; (c) the creation of duplicated sequence maintained on extrachromsomal DNA by addition of plasmids; and (d) the creation of duplicated sequence maintained on extrachromsomal DNA by addition of a bacterial artificial chromosome (BAC).

Integration methods may use site specific or homologous recombination.

Suicide vector methods are preferred as this will allow the addition of genes in stages and so the full merodiploid state can be built up iteratively in the course of several transformations.

Transposon Mutagenesis

Transposons, sometimes called transposable elements, are mobile polynucleotides. The term transposon is well known to those skilled in the art and includes classes of transposons that can be distinguished on the basis of sequence organisation, for example short inverted repeats at each end; directly repeated long terminal repeats (LTRs) at the ends; and polyA at 3'ends of RNA transcripts with 5' ends often truncated.

Transposomes are transposase-transposon complexes wherein the transposon does not encode transposase. Thus, once inserted the transposon is stable. Preferably, in order to ensure mutant pool stability, the transposon does not encode transposase and is provided in the form of a transposome (i.e. as a complex with transposase enzyme), as described below.

The transposon/transposome can be introduced into genomic and/or plasmid DNA within bacterial cells by any of a wide variety of standard procedures which are well-known to those skilled in the art. For example, transposomes can be introduced by electroporation (or any other suitable transformation method).

Preferably, the transformation method generates $1 \times 10^3$ to $5 \times 10^3$ transformants/ng DNA, and such transformation efficiencies are generally achievable using electroporation.

Alternatively, transposon mutagenesis may be performed in vitro and recombinant molecules transformed/transfected into bacterial cells. In such embodiments, transposomes can be prepared according to a standard protocol by mixing commercially available transposase enzyme with the transposon DNA fragment. The resulting transposomes are then mixed with plasmid DNA of the plasmid of interest to allow transposition, then the DNA introduced into a host bacterial strain using electrotransformation to generate a pool of plasmid transposon mutants.

In embodiments where mutagenesis is performed in vitro, it is possible to mix transposomes with genomic DNA in vitro and then introduce the mutagenized DNA (optionally, after fragmentation and/or circularization) into the host bacterial strain (e.g. by electroporation) whereupon endogenous recombination machinery incorporates it into the genome. Such an approach may be particularly useful in the case of bacteria which are naturally competent (e.g. *Acinetobacter* spp.) and/or can incorporate DNA via homologous crossover (e.g. double crossover) recombination events.

In the methods of the invention, the $Ab^R$ mutant is transformed with: (i) one or more essential genes of said bacterium; and (ii) a transposon which insertionally inactivates bacterial DNA, to produce a pool of transposon mutants which are merodiploid for said one or more essential genes. The $Ab^R$ mutant may be: (a) transformed simultaneously with the one or more essential genes of said bacterium and the transposon; (b) first transformed with the transposon and then with the one or more essential genes of said bacterium; or (c) first transformed with the one or more essential genes of said bacterium and then with the transposon.

When the $Ab^R$ mutant is transformed simultaneously with the one or more essential genes of said bacterium and the transposon, or first transformed with the one or more essential genes of said bacterium and then with the transposon, undesired transposon insertion into the introduced essential genes may occur which can reduce the efficiency of merodiploid formation and complicate the analysis of the data obtained from such libraries.

Such problems are avoided when the $Ab^R$ mutant is first transformed with the transposon and then with the one or more essential genes of said bacterium. However, depending on the efficiency of the process used to introduce the essential gene(s), such a strategy may require a significantly larger number of transformation experiments to give a library of sufficient size. An alternative solution exploits the phenomenon of transposition immunity. Here, undesirable transposition into the introduced essential genes is eliminated (or reduced) by incorporating transposon repeat sequences into extrachromosomal DNA (typically, plasmid or BAC) bearing the essential genes used to create the merodiploids. Such a strategy may be used in conjunction with transposons based on, for example, Tn3 or its relatives, as described below.

Transposons for Use in the Methods of the Invention

Any suitable transposon may be used in the methods of the invention. Suitable transposons include those based on Tn3 and the Tn3-like (Class II) transposons including γδ (Tn1000), Tn501, Tn2501, Tn21, Tn917 and their relatives. Also Tn10, Tn5, TnphoA, Tn 903, bacteriophage Mu and related transposable bacteriophages. A variety of suitable transposons are also available commercially, including for example the EZ-Tn5™<R6Kγori/KAN-2> transposon.

Preferred transposons are those which carry antibiotic resistance genes (which may be useful in identifying mutants which carry a transposon) including Tn5, Tn10 and TnphoA. For example, Tn10 carries a tetracycline resistance gene between its IS elements while Tn5 carries genes encoding polypeptides conferring resistance to kanamycin, streptomycin and bleomycin. Other suitable resistance genes include those including chloramphenicol acetyltransferase (conferring resistance to chloramphenicol).

It is of course possible to generate new transposons by inserting different combinations of antibiotic resistance genes between IS elements, or by inserting combinations of antibiotic resistance genes between transposon mosaic ends (preferred), or by altering the polynucleotide sequence of the transposon, for example by making a redundant base substitution, or any other type of base substitution that does not affect the transposition or the antibiotic resistance characteristics of the transposon, in the coding region of an antibiotic resistance gene or elsewhere in the transposon. Such transposons are included within the scope of the invention.

In many embodiments, a single transposon is used to generate the mutant pool. However, as explained above, the number of Tn insertion mutants (i.e. the mutant pool size) required to achieve a comprehensive pool or library depends inter alia on any Tn insertion site bias. Thus, in cases where the transposon insertion site bias occurs, two or more different transposons may be used in order to reduce or eliminate insertion site bias. For example, a combination of two different transposons based on Tn5 and Tn10 may be employed.

Figure 2:
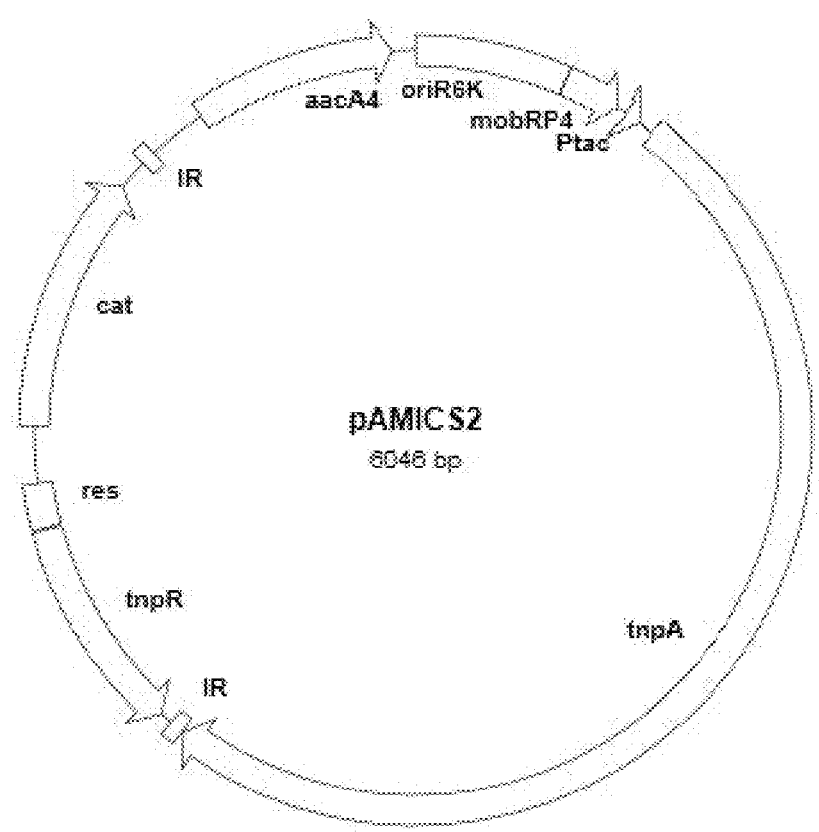
FIG. 2 is a graphical illustration showing the transposon delivery plasmid pAMICS2.

Suitable transposon systems for use in methods which exploit the phenomenon of transposition immunity (as described above) include those based on Tn3 and its relatives. For example, the transposon delivery plasmid pAM-ICS2 (see FIG. 2) contains the entire Tn3-based transposon-generating system (including genes encoding the resolvase and transposase enzymes, TnpR and TnpA) and an origin of replication (oriR6K) that functions only in certain E. coli strains that possess the pir gene, thus preventing propagation in the receiving bacteria after transposition. The plasmid also contains the mobilisation origin (mobRP4) to allow transfer from a donor strain, which is permissive to plasmid replication (i.e. contains the pir gene) and that possesses the RP4 plasmid transfer functions, by conjugation. Inadvertent propagation of the plasmid can be detected, if transposition doesn't occur, by the presence of a tobramycin resistance gene (aacA4).

Thus, in another aspect of the invention there is provided a method for identifying a gene (for example an essential gene) which serves as an antibiotic target in a bacterium, the method comprising the steps of:
  (a) transforming bacteria with an extrachromosamal element (e.g. plasmid or BAC) comprising: (i) one or more essential genes of said bacterium; and (ii) one or more transposon repeat sequences, to produce a pool of bacteria which are merodiploid for said one or more essential genes; and
  (b) transforming the merodiploids of step (a) with a transposon delivery plasmid comprising: (i) gene encoding a transposase and a resolvase; and (ii) invert repeat transposase recognition sites;
wherein the one or more transposon repeat sequences of the extrachromosomal element of step (a) confer transposon immunity against the transposon delivered by the plasmid of step (b).

In this aspect of the invention, the transposon delivery system is preferably based on Tn3, for example containing the Tn3 tnpA and tnpR genes. Preferred are transposon delivery plasmids which further comprise one or more antibiotic resistance gene(s).

Determining the Distribution of Transposon Insertions

The distribution of transposon insertions is preferably determined by sequencing bacterial DNA adjacent or near (5' and/or 3') the insertion site (e.g. by sequencing DNA which comprises transposon-genomic DNA junctions). Typically, bacterial DNA flanking or adjacent one or both ends of the transposon is sequenced.

The length of adjacent DNA sequenced need not be extensive, and is preferably relatively short (for example, less than 200 base pairs).

Various methods can be used to determine the transposon insertion distribution using DNA sequencing: such methods have recently been dubbed Tn-seq procedures (van Opijnen et al. (2009) Nat. Methods 6: 767-772). For example, Tn-seq procedures include affinity purification of amplified Tn junctions (Gawronski et al. (2009) PNAS 106: 16422-16427); ligation of adaptors into genome sequences distal to the end of the transposon using a specialized restriction site (Goodman et al. (2009) Cell Host Microbe 6: 279-289; van Opijnen et al. (2009) Nat. Methods 6: 767-772); selective amplification (Langridge et al. (2009) Genome Research 19: 2308-2316) and the generation of single-stranded DNA circles bearing Tn junctions, which serve as templates for amplification and sequencing after elimination of genomic DNA by exonuclease digestion (Gallagher et al. (2011) mBio 2(1):e00315-10).

Any suitable high-throughput sequencing technique can be used, and there are many commercially available sequencing platforms that are suitable for use in the methods of the invention. Sequencing-by-synthesis (SBS)-based sequencing platforms are particularly suitable for use in the methods of the invention: for example, the Illumina™ system generates millions of relatively short sequence reads (54, 75 or 100 bp) and is particularly preferred.

Other suitable techniques include methods based on reversible dye-terminators. Here, DNA molecules are first attached to primers on a slide and amplified so that local clonal colonies are formed (bridge amplification). Four types of ddNTPs are added, and non-incorporated nucleotides are washed away. Unlike pyrosequencing, the DNA can only be extended one nucleotide at a time. A camera takes images of the fluorescently labeled nucleotides then the dye along with the terminal 3' blocker is chemically removed from the DNA, allowing a next cycle.

Other systems capable of short sequence reads include SOLiD™ and Ion Torrent technologies (both sold by Applied Biosystems™). SOLiD™ technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. The result is sequences of quantities and lengths comparable to Illumina sequencing.

Ion Torrent Systems Inc. have developed a system based on using standard sequencing chemistry, but with a novel, semiconductor based detection system. This method of sequencing is based on the detection of hydrogen ions that are released during the polymerisation of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

Functional Assessment of Putative Essential Genes

The putative essential gene identified by comparing the distribution of transposon insertions between test cultures may be further characterized by various techniques which directly or indirectly assess its function. In this way, an essential function may be definitively assigned to said putative essential gene.

Suitable techniques include bioinformatics, where the (full or partial) sequence of the putative essential gene is used to interrogate sequence databases containing information from the bacterium assayed and/or other species in order to identify genes (e.g. orthologous genes in other species) for which essential biochemical function(s) have already been assigned and/or which have been shown to be essential.

Suitable bioinformatics programs are well known to those skilled in the art and include the Basic Local Alignment Search Tool (BLAST) program (Altschul et al. (1990) J. Mol. Biol. 215: 403-410 and Altschul et al. (1997) Nucl. Acids Res. 25: 3389-3402). Suitable databases include, for example, EMBL, GENBANK, TIGR, EB SWISS-PROT and trEMBL.

Alternatively, or in addition, the (full or partial) sequence of the putative essential gene is used to interrogate a sequence database containing information as to the identity of essential genes which has been previously constructed using the conventional Tn-seq methods described in the prior art (e.g. as described in Gawronski et al. (2009) PNAS 106: 16422-16427; Goodman et al. (2009) Cell Host Microbe 6: 279-289; van Opijnen et al. (2009) Nat. Methods 6: 767-772; Langridge et al. (2009) Genome Research 19: 2308-2316; Gallagher et al. (2011) mBio 2(1):e00315-10) and/or the techniques described in WO 01/07651 (the contents of which are hereby incorporated by reference).

Alternatively, or in addition, essentiality can be imputed by eliminating the possibility that a putative essential gene acts as an antibiotic resistance gene. For example, the (full or partial) sequence of the putative essential gene is used to interrogate sequence databases containing sequence information of genes previously identified as antibiotic resistance genes using the Tn-seq methods described in e.g. Gawronski et al. (2009) PNAS 106: 16422-16427; Goodman et al. (2009) Cell Host Microbe 6: 279-289; Langridge et al. (2009) Genome Research 19: 2308-2316 or Gallagher et al. (2011) mBio 2(1):e00315-10. Antibiotic resistance genes may be identified in such methods as a class of niche-specific/conditionally essential genes.

Ancillary Analytic Methods

The methods of the invention may be used in conjunction with other techniques for identifying essential, conditionally essential, non-essential and/or essential genes serving as targets for antibiotics, as described below:

(a) Activating Tn-Seq

The method of the invention may optionally further comprise the steps of:
(a) generating a pool of mutant bacteria by transposon mutagenesis with an activating transposon ($Tn_A$), wherein the $Tn_A$ comprises a promoter such that transposon insertion into bacterial DNA increases the transcription of a gene at or near the insertion site;
(b) growing bacteria from the mutant pool in the presence of different amounts of said antibiotic to produce two or more test cultures; and
(c) comparing the distribution of $Tn_A$ insertions between test cultures to identify a putative essential gene serving as a target of said antibiotic in said bacterium.

The use of an activating transposon ensures that transposon insertions into essential genes are represented in the initial mutant pool, since transposon insertion can now result in gene activation rather than insertional inactivation. Thus, the effect of the presence of antibiotic during subsequent culture of the mutant pool on transposon distribution can be studied (and the identity of the gene target(s) thereby determined).

As used herein, the term "activating transposon" (hereinafter abbreviated "$Tn_A$") defines a transposon which comprises a promoter such that transposon insertion increases the transcription of a gene at or near the insertion site. Examples of such transposons are described in Troeschel et al. (2010) Methods Mol Biol. 668:117-39 and Kim et al. (2008) Curr Microbiol. 57(4): 391-394.

The activating transposon/transposome can be introduced into genomic and/or plasmid DNA within bacterial cells by any of a wide variety of standard procedures which are well-known to those skilled in the art. For example, $Tn_A$ transposomes can be introduced by electroporation (or any other suitable transformation method).

Any suitable activating transposon may be used in the methods of the invention. Suitable transposons include those based on Tn3 and the Tn3-like (Class II) transposons including γδ (Tn1000), Tn501, Tn2501, Tn21, Tn917 and their relatives. Also Tn10, Tn5, TnphoA, Tn 903, bacteriophage Mu and related transposable bacteriophages. A variety of suitable transposons are also available commercially, including for example the EZ-Tn5™<R6Kγori/KAN-2> transposon.

Preferred transposons are those which carry antibiotic resistance genes (which may be useful in identifying mutants which carry a transposon) including Tn5, Tn10 and TnphoA. For example, Tn10 carries a tetracycline resistance gene between its IS elements while Tn5 carries genes encoding polypeptides conferring resistance to kanamycin, streptomycin and bleomycin. Other suitable resistance genes include those including chloramphenicol acetyltransferase (conferring resistance to chloramphenicol).

It is of course possible to generate new transposons by inserting different combinations of antibiotic resistance genes between IS elements, or by inserting combinations of antibiotic resistance genes between transposon mosaic ends (preferred), or by altering the polynucleotide sequence of the transposon, for example by making a redundant base substitution in the coding region of an antibiotic resistance gene or elsewhere in the transposon, or any other type of base substitution that does not affect the transposition or the antibiotic resistance characteristics of the transposon, in the coding region of an antibiotic resistance gene or elsewhere in the transposon. Such transposons are included within the scope of the invention.

In many embodiments, a single transposon is used to generate the mutant pool. However, as explained above, the number of Tn insertion mutants (i.e. the mutant pool size) required to achieve a comprehensive pool or library depends inter alia on any Tn insertion site bias. Thus, in cases where the transposon insertion site bias occurs, two or more different transposons may be used in order to reduce or eliminate insertion site bias. For example, a combination of two different transposons based on Tn5 and Tn10 may be employed.

Promoters for Use in Activating Transposons

The nature of the promoter present in the $Tn_A$ is dependent on the nature of the transposon and the ultimate bacterial host. Generally, an efficient, outward-oriented promoter which drives high level transcription of DNA near or adjacent to the insertion site is chosen.

The promoter may include: (a) a Pribnow box (−10 element); (b) a −35 element and/or (c) an UP-element.

For example, the lac promoter can be used with the EZ-Tn5™<R6Kγori/KAN-2> transposon, and such constructs are suitable for assay of e.g. *Escherichia coli, Enterobacter* spp. and other members of the family Enterobacteriaceae such as *Klebsiella* spp. Other suitable promoters include: rpl/J (large ribosomal subunit protein; moderate strength promoter); tac (artificial lac/trp hybrid; strong promoter) and rrnB (ribosomal RNA gene promoter; very strong promoter). The sequences of the latter promoters are shown below:

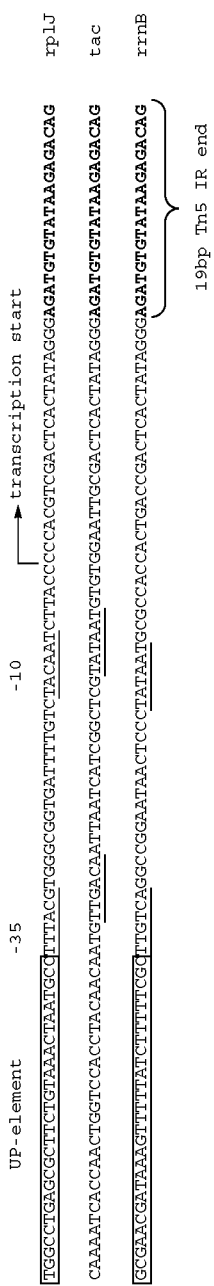

SEQ ID NOs:1, 2 and 3, respectively

In the optional further steps set out above:
the mutant pool may comprise at least $0.5\times10^5$ mutants, for example at least $1\times10^5$ mutants;
the mutant pool may comprise at least $5\times10^5$ mutants;
the mutant pool may comprise at least $1\times10^6$ mutants;
the mutant pool may comprises $0.5\times10^6$ to $2\times10^6$ mutants;
the mutant pool may comprise about $1\times10^6$ mutants;
transformation with the transposon in step (b) may yield an insertion rate of at least one transposon per 50 base pairs of bacterial DNA, at least one transposon per 30 base pairs of bacterial DNA, at least one transposon per 25 base pairs of bacterial DNA, at least one transposon per 15 base pairs of bacterial DNA or at least one transposon per 10 base pairs of bacterial DNA;
the bacterial DNA of step (b) may be genomic DNA, plasmid DNA or a mixture of genomic and plasmid DNA;
the transposon mutagenesis of step (a) may occur in vivo or in vitro;
the bacterium may be a Gram-positive bacterium;
the bacterium may be selected from *Enterococcus faecalis*, *Enterococcus faecium* and *Neisseria gonorrhoeae*;
the bacterium may be a Gram-negative bacterium;
the bacterium may be selected from: *Klebsiella pneumoniae*, *Acinetobacter baumanii*, *Escherichia coli*, *E. coli* ST131 strains, *Pseudomonas aeruginosa*, *Enterobacter cloacae*, *Enterobacter aerogenes* and *Neisseria gonorrhoeae*;
bacteria may be grown from the mutant pool in step (b) by inoculating growth medium with $10^7$ to $10^9$, for example about $10^8$, cfu from the mutant pool;
bacteria may be grown from the mutant pool in step (b) in the presence of antibiotic at a concentration of about 0.5, about 1 and about 2×MIC to produce at least three test cultures;
the distribution of $Tn_A$ insertions between test cultures may be compared by sequencing DNA adjacent or near the insertion site of the $Tn_A$;
the sequencing of DNA adjacent or near the insertion site of the $Tn_A$ may comprise selective amplification of transposon-bacterial DNA junctions;
the sequencing may comprise sequencing-by-synthesis (SBS) biochemistry;
about 25, 50, 75, 100 or greater than 100 base pairs of DNA adjacent or near the $Tn_A$ insertion site may be sequenced; and/or
the sequenced DNA may be 5' and/or 3' to the $Tn_A$ insertion site.

(b) Tn-Seq

The method of the invention may optionally further comprise the steps of Tn-seq analysis as described in e.g. Gawronski et al. (2009) PNAS 106: 16422-16427; Goodman et al. (2009) Cell Host Microbe 6: 279-289; Langridge et al. (2009) Genome Research 19: 2308-2316 or Gallagher et al. (2011) mBio 2(1):e00315-10. When used in combination with Tn-seq analysis, the invention may further identify: (a) essential genes; (b) genes advantageous (but not essential) for growth; (c) genes disadvantageous for growth under particular conditions; and (d) genes involved in conferring tolerance to certain conditions ("niche-specific" essential genes), in addition to essential genes which serve as antibiotic targets.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Step 1: Production of Mutant Antibiotic Resistant Clones ($Ab^R$ Mutants)

The MIC of the antibiotic to be tested is determined for the bacterium of interest. Relative bacterial insensitivity to the antibiotic is then generated by either of the following methods:

Method 1

Bacteria are grown in 100 ml cultures through serial passages in antibiotic concentrations of 0.5, 1, 2, 4, 8, 16 and 32×MIC until bacteria are selected which grow in significantly higher antibiotic concentrations than those in the wild type starting cultures.

Method 2

Bacteria grown to log phase are harvested and resuspended at different cell densities (i.e. $1\times10^7$, $1\times10^8$, $1\times10^9$, $1\times10^{10}$ and $1\times10^{11}$ cells/ml) in broth containing antibiotic concentrations of 0.5, 1, 2, 4, 8, 16 and 32×MIC before being plated out on agar plates containing the same antibiotic concentrations. Bacterial clones with reduced antibiotic sensitivity have their resistance profile confirmed by further growth at high antibiotic concentrations.

Several different antibiotic insensitive clones, generated using either Method 1 or Method 2 or both Method 1 and Method 2, are then selected for transposon mutagenesis and each grown separately in 2×TY broth, with maintenance concentrations of antibiotic to an $OD_{600}$ of 0.3-0.5. Cells are then harvested and washed three times in ½ original culture volume 10% glycerol and resuspended in ¹⁄₁₀₀₀ original culture volume of 10% glycerol and stored at −80° C.

Step 2: Preparation of Transposomes

Transposon DNA (EZ-Tn5<R6Kγori/KAN-2>) is amplified using oligonucleotides 5'-CTGTCTCTTATACA-CATCTCCCT (SEQ ID NO: 4) and 5'-CTGTCTCTTATA-CACATCTCTTC (SEQ ID NO: 5) with Pfu Ultra Fusion II, (Stratagene). The resultant amplicon is then phosphorylated using polynucleotide kinase (New England Biolabs). Two hundred nanograms of this DNA are then incubated with EZ-Tn5 transposase (Epicenter Biotechnologies) at 37° C. for 1 h then stored at −20° C. at a concentration of 20 ng/µl.

Step 3: Preparation of Vector Comprising Essential Genes

A bacterial self-replicating plasmid containing the ampicillin-resistance gene is made containing the wild type essential genes identified using data obtained from a previous Tn-seq analysis carried out using TraDIS (see Langridge et al. (2009) Genome Research 19: 2308-2316) or published data. Purified plasmid DNA is diluted to 20 ng/µl and stored at −80° C.

Step 4: Production of a Merodiploid Tn:$Ab^R$ Mutant Pool

A merodiploid Tn:$Ab^R$ mutant pool is prepared from each of the several different antibiotic insensitive clones. In each case:

Sixty microliters of $Ab^R$ mutant cells (previously stored at −80° C. in Step 1) are mixed with 0.2 µl (4 ng) of transposomes (as prepared in Step 2) and 1 µl (20 g) of the expression vector (as prepared in Step 3) and electrotransformed in a 2 mm electrode gap cuvette using a Bio-Rad GenePulser II set to 2.4 kV, 25 µF, and 200Ω.

Transformed cells are resuspended in 1 mL of SOC medium (Invitrogen) and incubated at 37° C. for 2 h then spread on L-agar supplemented with 50 mg/ml ampicillin and 7.5 mg/ml kanamycin.

After incubation overnight at 37° C., the number of colonies on several plates is estimated by counting a proportion of them, and from this the total number of colonies on all plates is estimated conservatively. Kanamycin/Ampicillin resistant colonies are harvested by resuspension in sterilized deionized water using a bacteriological spreader.

Resuspended cells from 10-20 electroporations then are pooled to create a pool of merodiploid $Ab^R$ transposon mutants ($Tn:Ab^R$ mutants) estimated to include over 1 million transposon mutants. The efficiency of transformation using this technique decreases as the size of the expression plasmid is increased, which means more than 20 electroporations may be required for very large expression plasmids.

Conjugation is an alternative method to transformation for the introduction of DNA into bacterial cells. Conjugation may be used to introduce a vector DNA comprising the transposon mentioned in Step 2, and a vector DNA comprising one or more essential genes mentioned in Step 3. Donor and recipient strains are mixed, either by cross-streaking on solid growth medium or by mixing appropriate volumes of liquid broth cultures, which may be 0.5 ml, of the donor and recipient strains. After incubation for several hours, which may be 1 hour to 16 hour at an appropriate temperature, which may be room temperature (20-24° C.), 30° C. or 37° C. the bacteria are spread on solid growth medium supplemented with an antibiotic that selects for the donated DNA and an antibiotic that selects for the recipient bacterial strain. The incubation temperature for the conjugation is determined according to the DNA being introduced: a lower temperature is appropriate for DNA comprising the transposon if transposition of the transposon is optimal at this temperature. Suitable strains that could act as donor in the conjugation include E. coli strain SM10λpir which carries the pir gene to mediate replication of any DNA vector comprising the oriR6K replication origin, such as a DNA vector comprising the transposon, and also carries the transfer functions from plasmid RP4 that mediates transfer of any vector DNA comprising the mobilisation origin mobRP4.

Step 5: Determining Antibiotic Target Gene(s)

Four cultures of 100 ml broth medium are prepared, two of which are supplemented with the antibiotic at a concentration 1 to 4×MIC (this depends on the antibiotic insensitivity of the original bacterial clone). Assuming a transposon mutant library of 1 million mutants, ~$10^8$-$10^9$ cfu from the merodiploid $Tn:Ab^R$ mutant pool of Step 4 are used to inoculate each culture.

Cultures are grown to stationary phase and cells harvested for genomic DNA extraction. Fresh cultures are also prepared and inoculated with $10^8$-$10^9$ cfu from the first cultures. These are grown to stationary phase and cells harvested for extraction of genomic DNA. Genomic DNA is sequenced using the TraDIS method (see Langridge et al. (2009) Genome Research 19: 2308-2316) to obtain sequence reads initiated from the transposon insertion sites.

Sequence reads are then mapped to the bacterial genome sequence and compared with the genome annotation to determine the number of sequence reads that map to each gene for the 4 cultures (2 test and 2 control). Comparison of the control data sets with each other and of test data sets with each other indicates the degree of experimental variation. Comparison of control data with test data sets shows experimental reproducibility and indicates gene(s) targeted by the antibiotic. Illumina™ sequence reads from transposon insertion within the essential gene antibiotic target gene(s) would occur in cells grown without antibiotic, but not cells grown in antibiotic.

Antibiotic resistance genes, identified using a wild type "standard" TraDIS library grown in suboptimal antibiotic concentration, can be excluded as potential antibiotic target genes (see below).

If instead of using a complementation plasmid containing all essential genes, plasmids containing specific collections of essential genes or chromosomal fragments are used, then more bioinformatic statistical deconvolution is required for antibiotic target identification. The putative identity of the complementing genes and the antibiotic target genes would be determined from detailed analysis of transposon read densities with and without antibiotic.

Exclusion of Antibiotic Resistance Genes

Conventional transposon directed insertion-site sequencing (TraDIS—see Langridge et al. (2009) Genome Research 19: 2308-2316) can be used to identify antibiotic resistance genes which are not essential to growth under normal conditions but which confer tolerance to the antibiotic (i.e. a class of the "niche-specific" essential genes discussed in Langridge et al. (2009)). This permits the elimination of antibiotic resistance genes from candidate antibiotic target genes, as described below.

The MIC of the antibiotic to be tested is determined for the bacterium of interest. Four cultures of 100 ml broth medium are prepared, two of which are supplemented with the antibiotic at a concentration 0.5 to 0.75×MIC (i.e. just below MIC). Assuming a transposon mutant pool of 1 million mutants, $10^8$-$10^9$ cfu of the pool are used to inoculate each culture. Cultures are grown to stationary phase and cells harvested for genomic DNA extraction. Fresh cultures are also prepared and inoculated with $10^8$-$10^9$ cfu from the first cultures. These are grown to stationary phase and cells harvested for extraction of genomic DNA. Genomic DNA is sequenced using the Illumina™ platform incorporating the TraDIS modification to obtain sequence reads initiated from the transposon insertion sites. Sequence reads are then mapped to the bacterial genome sequence and compared with the genome annotation to determine the number of sequence reads that map to each gene for the 4 cultures (2 test and 2 control).

Comparison of the control data sets with each other and of test data sets with each other indicates the degree of experimental variation. Comparison of control data with test data sets shows experimental reproducibility and indicates genes that are involved in resistance.

FIG. 1 shows the results of a pilot study to identify genes that contribute to ciprofloxacin resistance in Salmonella Typhi. The graph includes data for every non-essential gene in the bacterium's genome. The transposon insertion library was grown in 4 conditions: 2 control cultures (no antibiotic) and 2 cultures each with a sub-IMIC concentration of ciprofloxacin. Each point represents a gene and each gene is plotted 3 times (ctrl1 v ctrl 2 & CIP1 v CIP2=black and indicates the degree of experimental variation; CIP mean v ctrl mean=grey; grey points that plot beyond the cluster of black control points represent genes for which data shows significant difference). These comparisons provide a measure of the amount of experimental variation. Grey points are an average of the control data compared to the test data. In FIG. 1, grey points below the diagonal cluster of black points are genes that contribute to resistance. The further from the black cluster the grey points are, the more significant the data. Genes that are known to contribute to ciprofloxacin resistance in Salmonella are found in this region of the graph, as well as genes not previously known to contribute to resistance. Grey points above the black cluster are genes that contribute to sensitivity. Again, genes known to contribute to sensitivity are found in this region of the graph, and this data identifies genes not previously known to contribute to sensitivity. Data are generally sufficiently clear so as not to require statistical analysis.

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method for identifying a putative essential gene which serves as an antibiotic target in a bacterium, the method comprising the steps of:
   (a) generating an antibiotic resistant mutant of said bacterium by a method comprising the step of selecting for growth in the presence of said antibiotic to produce an antibiotic resistant mutant clone ($Ab^R$ mutant);
   (b) transforming the $Ab^R$ mutant with: (i) one or more wild-type copies of essential genes of said bacterium; and (ii) a transposon which insertionally inactivates bacterial DNA, to produce a pool of transposon mutants which are merodiploid for said one or more essential genes;
   (c) growing bacteria from the merodiploid pool in the presence of different amounts of said antibiotic to produce two or more test cultures, wherein transposon insertions into an essential gene serving as an antibiotic target in the bacterial DNA are represented under non-selective conditions but not under selective conditions, and wherein one amount of said antibiotic is non-selective and another amount of said antibiotic is selective; and
   (d) comparing the distribution of transposon insertions between test cultures to identify a putative essential gene serving as a target of said antibiotic in said bacterium.

2. The method of claim 1 wherein the merodiploid pool comprises at least $0.5 \times 10^5$ mutants.

3. The method of claim 1 wherein the merodiploid pool comprises at least $5 \times 10^5$ mutants.

4. The method of claim 1 wherein the merodiploid pool comprises at least $1 \times 10^6$ mutants.

5. The method of claim 1 wherein the merodiploid pool comprises $0.5 \times 10^6$ to $2 \times 10^6$ mutants.

6. The method of claim 5 wherein the merodiploid pool comprises about $1 \times 10^6$ mutants.

7. The method of claim 1 wherein transformation with the transposon in step (b) yields an insertion density of at least one transposon per 50 base pairs of bacterial DNA.

8. The method of claim 1 wherein transformation with the transposon in step (b) yields an insertion density of at least one transposon per 30 base pairs of bacterial DNA.

9. The method of claim 1 wherein transformation with the transposon in step (b) yields an insertion density of at least one transposon per 25 base pairs of bacterial DNA.

10. The method of claim 1 wherein transformation with the transposon in step (b) yields an insertion density of at least one transposon per 15 base pairs of bacterial DNA.

11. The method of claim 1 wherein transformation with the transposon in step (b) yields an insertion density of at least one transposon per 10 base pairs of bacterial DNA.

12. The method of claim 1 wherein the bacterial DNA of step (b) is genomic DNA.

13. The method of claim 1 wherein the bacterial DNA of step (b) is plasmid DNA or a mixture of genomic and plasmid DNA.

14. The method of claim 1 wherein in step (b) the $Ab^R$ mutant is first transformed with the one or more essential genes of said bacterium and then with the transposon.

15. The method of claim 14 wherein in step (b) the $Ab^R$ mutant is first transformed with an extrachromosomal element comprising: (i) one or more essential genes of said bacterium; and (ii) one or more transposon repeat sequences; and then transformed with a transposon delivery plasmid comprising: (i) a gene encoding a transposase; and (ii) invert repeat transposase recognition sites; wherein the one or more transposon repeat sequences of the extrachromosomal element confer transposon immunity against the transposon delivered by the transposon delivery plasmid.

16. The method of claim 2 wherein the merodiploid pool comprises at least $1 \times 10^5$ mutants.

17. The method of claim 15, wherein the extrachromosomal element is a BAC or plasmid.

18. The method of claim 15, wherein the $Ab^R$ mutant is transformed in step (ii) by conjugation with a donor bacterium.

* * * * *

```
                              SEQUENCE LISTING

<160> NUMBER OF SEQ ID NOS: 5

<210> SEQ ID NO 1
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 1
tggcctgagc gcttctgtaa actaatgcct ttacgtgggc ggtgattttg tctacaatct      60 taccccacg tcgactcact atagggagat gtgtataaga gacag                      105

<210> SEQ ID NO 2
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 2
caaaatcacc aactggtcca cctacaacaa tgttgacaat taatcatcgg ctcgtataat      60
gtgtggaatt gcgactcact atagggagat gtgtataaga gacag                     105

<210> SEQ ID NO 3
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 3
gcgaacgata aagtttttat cttttttcgct tgtcaggccg gaataactcc ctataatgcg     60
ccaccactga ccgactcact atagggagat gtgtataaga gacag                     105

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
ctgtctctta tacacatctc cct                                              23

<210> SEQ ID NO 5
<211> LENGTH: 23
<212> TYPE: DNA
```

```
<213> ORGANISM: Artificial Sequence
<220> FEATURE:
<223> OTHER INFORMATION: Synthetic oligonucleotide

<400> SEQUENCE: 5
ctgtctctta tacacatctc ttc                                              23
```